United States Patent [19]

Carter et al.

[11] Patent Number: 5,142,084
[45] Date of Patent: Aug. 25, 1992

[54] PREPARATION OF ALLYLPHOSPHONIC ACID

[76] Inventors: Charles G. Carter, 9524 Bruce Dr., Silver Spring, Md. 20901; David R. Sterrenburg, 1126 S. 12th St., Manitowoc, Wis. 54220

[21] Appl. No.: 775,885

[22] Filed: Oct. 11, 1991

[51] Int. Cl.⁵ .............................. C07F 9/38; C07F 9/40
[52] U.S. Cl. ........................................ 558/88; 558/217
[58] Field of Search ........................ 558/88, 131, 217

[56] References Cited

U.S. PATENT DOCUMENTS 4,017,564 4/1977 Arend et al. ........................ 558/125
4,633,005 12/1986 Nalewajek et al. ................ 558/125

Primary Examiner—Mary C. Lee
Assistant Examiner—Michael G. Ambrose
Attorney, Agent, or Firm—Beverly K. Johnson

[57] ABSTRACT

A novel process for rearranging triallyl phosphite to diallyl allylphosphonate ester is disclosed. The process involves heating triallyl phosphite in the presence of a soluble, inorganic bromide or iodide catalyst. The rearrangement process is useful in a 3-step process for the preparation allylphosphonic acid from trialkyl phosphite without the isolation of intermediates.

23 Claims, No Drawings

5,142,084

PREPARATION OF ALLYLPHOSPHONIC ACID

FIELD OF THE INVENTION

This invention relates to a novel process for preparing allyl phosphonate ester by the catalytic rearrangement of triallyl phosphite. The process is useful as an intermediate step in a 3-step process for the preparation of allylphosphonic acid, which process involves (a) transesterfying a trialkyl phosphite with allyl alcohol to form triallyl phosphite; (b) catalytically rearranging the phosphite to form diallyl allylphosphonate ester; and (c) hydrolyzing the allylphosphonate ester to yield allylphosphonic acid.

BACKGROUND OF THE INVENTION

Allylphosphonic acid compounds have been used in a variety of applications such as, for example, flame retardants, plasticisers, lubricants, surfactants, water-treatment additives and as intermediates for various medicinal and agricultural products. Soviet Union Patent, SU 598,907, for example, discloses allylphosphonic acids which are useful as fire resistant polymers and are prepared by reacting alkali hypophosphite with allene to form the corresponding allylphosphonate alkali salt which is hydrolyzed to the allylphosphonic acid.

Typically, allylphosphonic acids are prepared by hydrolyzing corresponding esters of allylphosphonic acid in the presence of an acid catalyst. Esters of allylphosphonic acid have been prepared in a number of methods. German Patent DE 2,002,809 discloses allylphosphonic acid esters which have been prepared by a standard Arbuzov reaction of trialkylphosphite with allylbromide. This reaction provides dialkyl allylphosphonate in good yield; however, allylbromide is very expensive and presents health and ecological concerns as a volatile, highly reactive alkylating agent.

Allyl chloride has been substituted for allyl bromide in the Arbuzov reaction of a trialkyl phosphite and an allylhalide. For example, U.S. Pat. No. 4,017,564 issued to Arend et al. discloses a process for the production of allylphosphonic acid esters by reacting allyl chloride with trialkyl phosphite in the presence of an avalent and/or monovalent nickel catalyst. Yields obtained by this method are only moderate and a purification step is required to remove the transition metal catalyst. Allyl phosphonate esters have been prepared in poor yields by the reaction of allyl chloride with a sodium dialkyl phosphite. This process is described in Kosolapoff, J. Am. Chem. Soc., 73, 4040 (1951). In addition to unsatisfactory yields, prior art processes requiring allyl chloride present a hazard, since allyl chloride is very toxic and extremely volatile.

Allylphosphonate esters have also been prepared by several isomerization methods using a mixed tri-(allyl, alkyl) phosphite. In a method, as described in Lemper et al., Tet. Lett., 3053 (1964), the rearrangement has been carried out thermally at temperatures of greater than 200° C. The mixed phosphite has also been rearranged under triplet-sensitized photolysis in a quartz reactor using the procedure as described in Bentrude et at., J. Am. Chem. Soc., 109 (1987). The transformation has also been accomplished using nickel(0) catalyst as described in Lu et al., J. Organomet. Chem., 304, 239 (1986). These procedures are disadvantageous since they require special reaction conditions (i.e. high temperature, photolysis) or a transition metal catalyst. In addition, these procedures require the preparation and isolation of a mixed phosphite ester which preparation requires the use of potentially explosive phosphorochlorodites.

Trialkyl phosphites have been reported to undergo ester exchange with an allylic alcohol, see for example, Lemper et al., Tet. Lett., 3053 (1964). The use of an acid catalyst in such a process has also been described in Holy, Chem. and Ind., 721 (1965). The simultaneous transesterfication/rearrangement approach has also been reported for the conversion of triphenyl phosphite into an alkyl phosphonate, see for example, Laughlin, J. Org. Chem., 27, 3644 (1962) or Honig et al., J. Org. Chem., 42, 379 (1977). Such processes however, required reaction conditions of prolonged heating at temperatures in excess of 200° C.

It is one object of the present invention to provide a novel process for the rearrangement of triallyl phosphite to diallyl allylphosphonate ester. The process permits the rearrangement of triallyl phosphite under mild conditions without the use of high temperatures, photolysis, a transition metal catalyst or allyl halide.

Another object of the invention is to provide a simple and economical process of producing allylphosphonic acid from trialkyl phosphite in high yield and selectivity using inexpensive and readily-available starting reagents.

Other objects of the present invention will be evident from the ensuing description and appended claims.

SUMMARY OF THE INVENTION

The present invention is directed to a novel process of producing diallyl allylphosphonate ester by the catalytic rearrangement of triallyl phosphite. In accordance with the process of the invention, trialkyl phosphite is rearranged by heating the phosphite in the presence of a "catalytically effective" amount of a soluble, inorganic bromide or iodide compound for a period of time and at a temperature sufficient to obtain complete or substantially complete conversion of the triallyl phosphite to the diallyl allylphosphonate.

Another embodiment of this invention involves the use of the rearrangement process as an intermediate step in a series of three steps to unexpectedly provide a process of forming allyl phosphonic acid in high conversion and selectivity. According to this 3-step procedure, allylphosphonic acid is prepared by (a) transesterifying a trialkyl phosphite with allyl alcohol in the presence of an acid catalyst to form the corresponding triallyl phosphite; (b) rearranging triallyl phosphite by heating the phosphite in the presence of a soluble, inorganic bromide or iodide catalyst to form diallyl allylphosphonate ester; and (c) hydrolyzing the allylphosphonate ester to produce allylphosphonic acid. This process permits the preparation of allylphosphonic acid from allyl alcohol and trialkyl phosphite in a single reaction vessel without the isolation of intermediates.

DETAILED DESCRIPTION OF THE INVENTION

In accordance with the invention, triallyl phosphite is catalytically rearranged by heating the phosphite in the presence of a soluble, inorganic bromide or iodide catalyst for a period of time and at a temperature sufficient to produce the desired diallyl allyl phosphonate ester in adequate yield. The bromide or iodide catalyst is used in the rearrangement process in a "catalytically effective amount". As used herein, a "catalytically effective amount" is an amount of the bromide or iodide compound which is capable of catalyzing the rearrangement of triallyl phosphite to diallyl allylphosphonate ester to any extent. Generally, the amount of catalyst used is from about 0.1 to about 10 mole %, preferably about 0.5 to about 2.0 mole %, based on the amount of triallyl phosphite used.

Bromide and iodide compounds useful to catalyze the rearrangement process are soluble, inorganic bromide or iodide compounds selected from the group consisting of alkali metal bromides or iodides; tetraalkyl ammonium bromides or iodides; tetraalkyl phosphonium bromides or iodides; tetraaryl phosphonium bromides or iodides; or hydrogen bromide or hydrogen iodide, wherein any alkyl group has from 1 to 10, preferably 1 to 6 carbon atoms and any aryl group is phenyl or tolyl. Preferred catalysts include HX, NaX, KX, CsX, $R_4N^\oplus X^\ominus$ or $R'_4P^\oplus X^\ominus$ wherein X is Br or I; R is benzyl or an alkyl group having from 1 to 10, preferably 1 to 6, carbon atoms; and R' is benzyl, an alkyl group having from 1 to 10, preferably 1 to 6 carbon atoms, or an aryl group (such as phenyl, tolyl and the like). Most preferred catalysts are NaI, KI or HBr. For purposes of the invention the term "soluble" is used herein to indicate an inorganic bromide or iodide compound which is soluble in the reaction medium.

The temperature employed in the rearrangement process is critical and can be varied depending on factors known to those skilled in the art. The rearrangement will generally be carried out at a temperature greater than about 70° C. Temperatures within the range of from about 80° C. to about 150° C. are preferred. Most preferably, temperatures are within the range of 90° C. to about 125° C.

In accordance with the invention, the rearrangement process is carried out for a period of time sufficient to obtain complete or substantially complete conversion of triallyl phosphite to diallyl allylphosphonate. Reaction times are dependent to a significant degree upon the reaction temperature; the concentration and choice of catalyst; and other factors known to those skilled in the art. In general, reaction times can vary from about a few minutes to 24 hours or longer.

The rearrangement reaction may be carried out at atmospheric or sub-atmospheric pressure. For convenience the reaction is ran under an inert atmosphere to exclude water. In the alternative, the reaction may be ran open to the atmosphere in a vessel equipped with a means to exclude moisture, for example, a drying tube.

The rearrangement reaction may be ran without the addition of a solvent or an inert organic solvent may be used. Useful organic solvents include aromatic hydrocarbons such as toluene, benzene, xylene, chlorobenzene, benzonitrile and the like.

In a second embodiment of this invention, allylphosphonic acid (III) is prepared in a single pot reaction without the isolation of intermediates using a 3-step process. In a first step, triallyl phosphite is transesterfied with allyl alcohol to form triallyl phosphite (I). Triallyl phosphite is then rearranged to the diallyl allylphosphonate ester (II) in the second step using the process as described hereinabove. In the third step, diallyl allylphosphonate is hydrolyzed to allylphosphonic acid (III) using an aqueous acid medium.

The synthesis of allylphosphonic acid using this 3-step process is outlined below:

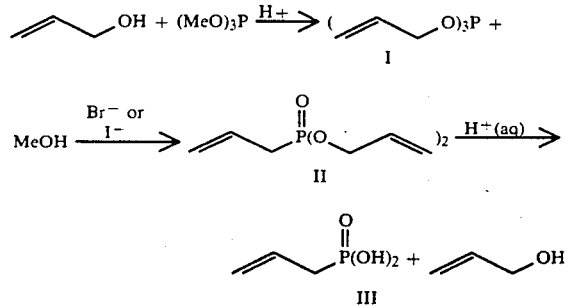

Transesterfication of the appropriate trialkyl phosphite with allyl alcohol is accomplished using the procedures such as described in Holy, Chem. and Ind., 721 (1965); Hoffmann et al., J. Am. Chem. Soc., 78, 5817 (1956); and Lemper et al., Tet. Let., 3053 (1964) which references are herein incorporated by reference. Preferably, the appropriate trialkyl phosphite is contacted with allyl alcohol in the presence of an acid catalyst at a temperature sufficient to distill the exchanging alcohol from the reaction mixture at the rate of its formation. The acid catalyst should be a strong acid, i.e. an acid having a pKa less than or equal to phosphoric acid. Preferably, the acid catalyst is hydrochloric acid. To obtain adequate yield of the transesterfication product, the molar ratio of the allyl alcohol to trialklyl phosphite should be from 3:1 to 10:1, preferably 3:1 to 5:1.

The transesterfication reaction is complete when no more of the exchanged alcohol distills off. Identification of the transesterfied triallyl phosphite product is accomplished using conventional techniques, such as gas chromatography and proton nuclear magnetic resonance (NMR) spectroscopy.

Trialkyl phosphites useful in the transesterfication reaction are those phosphites whose hydrolysis produce an alcohol having a boiling point less than or equal to allyl alcohol. Preferably, the trialkyl phosphite used in the transesterification are of the general formula

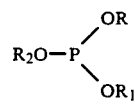

in which R, $R_1$ and $R_2$ are the same or different and are alkyl having from 1 to about 3 carbon atoms. Preferably, R, $R_1$ and $R_2$ are methyl, ethyl or isopropyl; most preferably, methyl or ethyl.

The resulting triallyl phosphite compound is used in the rearrangement process as described hereinabove without further purification or isolation. Completion of the rearrangement reaction and identification of the diallyl allylphosphonate ester is monitored by conventional techniques such as gas chromatography and NMR spectroscopy.

Hydrolysis of the allyl phosphonate ester is accomplished by contacting the ester with an aqueous acidic solution, preferably 2N to 6N hydrochloric acid, to provide allylphosphonic acid in good yield. The desired allyl phosphonic acid is isolated by the removal of water and allyl alcohol using any conventional technique, e.g. such as distillation.

The following examples are given for illustrative purposes only and are not meant to be a limitation on the invention as defined by the claims appended hereto.

EXAMPLE I

Sodium iodide (0.75 g, 5.0 mml) was added to a mixture of triallyl phosphite (65 g, 320 mml) and 34 g of allyl alcohol. The reaction mixture, kept under a nitrogen atmosphere to exclude moisture, was heated to 120° C. for 17 hours. Examination of the reaction product by gas chromatography showed that the triallyl phosphite had been completely converted to diallyl allylphosphonate.

EXAMPLE II

Transesterification

Trimethyl phosphite (62 g, 0.50 mole) was placed in a flask under a nitrogen atmosphere and a catalytic amount of concentrated HCl (0.16 g, 1.7 mmol) was added cautiously. Allyl alcohol (102.0 g, 1.76 mole) was charged into an addition funnel and 10 ml added to the reaction flask. The mixture was then heated to reflux (head temperature 65° C.). The remaining allyl alcohol was added gradually over a 4.5 hour period, while simultaneously distilling methanol through a 250 mm column packed with glass helices at a nominal 12.5:1 reflux ratio (when head temperature reached 67° C., the system automatically switched to total reflux until the head temperature dropped again). When allyl alcohol addition was complete, 83 ml cyclohexane was added to the pot to azeotropically distill out the remaining methanol (54° C., 64% cyclohexane). All material up to a head temperature of 65° C. was distilled in this manner. When GC analysis at this point indicated incomplete exchange, an additional 10 ml (0.147 mole) allyl alcohol and 12 ml cyclohexane were added and all materials below 74° C. distilled as before. The identity of the transesterification product formed after removal of the alcohols was confirmed to be triallyl phosphite by gas chromatography and proton nuclear magnetic resonance (NMR) spectroscopy.

Rearrangement

The triallyl phosphite prepared in the first step was used directly in the rearrangement without any purification or isolation. A catalytic amount of sodium iodide (0.75 g, 5 mmol) was added to the triallyl phosphite. The mixture was then heated at 120° C. for several hours until it was shown by gas chromatography that the reaction was complete. The identity of the product as diallyl allylphosphonate was confirmed by proton NMR spectroscopy.

Hydrolysis

The allylphosphonate ester produced in the previous step was hydrolyzed directly without isolation. Dilute hydrochloric acid (2N) was added with the simultaneous removal of water and allyl alcohol by distillation until the hydrolysis was complete. An additional portion of water was then added and distilled off to remove residual allyl alcohol. The produce was confirmed to be an aqueous solution of allylphosphonic acid (APA) by proton, carbon and phosphorus NMR spectroscopy. The overall yield of APA for the three-step sequence was 71%, (based on trimethyl phosphite charged).

WE CLAIM

1. A process for the preparation of diallyl allylphosphonate ester comprising heating triallyl phosphite in the presence of a catalytically effective amount of a soluble, inorganic bromide or iodide catalyst for a period of time and at a temperature sufficient to obtain diallyl allylphosphonate ester in good yield.

2. The process of claim 1 wherein the soluble, inorganic bromide or iodide catalyst is selected from the group consisting of alkali metal bromides or iodides; tetraalkyl ammonium bromides or iodides; tetraalkyl phosphonium bromides or iodides; tetraaryl phosphonium bromides or iodides; or hydrogen bromide or hydrogen iodide.

3. The process of claim 1 wherein the soluble, inorganic bromide or iodide catalyst is HX, NaX, KX, CsX, $R_4N^\oplus X^\ominus$ or $R'_4P^\oplus X^\ominus$ wherein X is Br or I; R is benzyl or alkyl; and R' is benzyl, alkyl or aryl.

4. The process of claim 3 wherein R and R' are alkyl having 1 to 6 carbon atoms.

5. The process of claim 3 wherein the bromide or iodide catalyst is NaI, KI or HBr.

6. The process of claim 1 wherein the amount of the catalyst is about 0.1 mole to about 10 mole percent based on the total moles of triallyl phosphite.

7. The process of claim 6 wherein the amount of the catalyst is from about 0.5 to about 2.0 mole percent based on the total moles of triallyl phosphite.

8. The process of claim 1 wherein the temperature is within the range of from about 80° C. to about 150° C.

9. The process of claim 8 wherein the temperature is within the range of from about 90° C. to about 125° C.

10. A process for producing allylphosphonic acid in improved yield and selectively comprising
    (a) transesterifying a trialkyl phosphite with allyl alcohol to form triallyl phosphite;
    (b) rearranging triallyl phosphite by heating in the presence of a soluble, inorganic bromide or iodide catalyst to form diallyl allylphosphonate; and
    (c) hydrolyzing diallyl allylphosphonate to obtain allylphosphonic acid.

11. The process of claim 10 wherein trialkyl phosphite is transesterified with allyl alcohol in the presence of a strong acid catalyst.

12. The process of claim 10 or 11 wherein allyl alcohol is transesterified with a trialkyl phosphite of the formula

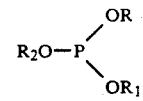

wherein R, $R_1$ and $R_2$ are the same or different and are alkyl having from 1 to 3 carbon atoms 13. The process of claim 10 wherein the soluble, inorganic bromide or iodide catalyst is selected from the group consisting of alkali metal bromides or iodides; tetraalkyl ammonium bromides or iodides; tetraalkyl phosphonium bromides or iodides; tetraaryl phosphonium bromides or iodides; or hydrogen bromide or hydrogen iodide.

14. The process of claim 10 wherein the soluble, inorganic bromide or iodide compound is HX, NaX, KX, CsX, $R_4N^\oplus X^\ominus$ or $R'_4P^\oplus X^\ominus$ wherein X is Br or I; R is benzyl or alkyl; and R' is benzyl, alkyl or aryl.

15. The process of claim 14 wherein R and R' are alkyl having from 1 to 6 carbon atoms.

16. The process of claim 10 wherein the amount of the catalyst is from about 0.1 mole to about 10 mole percent based on the total moles of triallyl phosphite.

17. The process of claim 16 wherein amount of the catalyst is from about 0.5 mole to about 2.0 moles percent based on the total moles of triallyl phosphite.

18. The process of claim 10 wherein triallyl phosphite is heated at a temperature within the range of from about 80° C. to about 150° C.

19. The process of claim 10 wherein the ratio of allyl alcohol transesterified with trialkyl phosphite is 3:1 to 10:1.

20. The process of claim 19 wherein the ratio of allyl alcohol to trialkyl phosphite is 3:1 to 5:1.

21. The process of claim 10 wherein diallyl allylphosphonate is hydrolyzed in an aqueous acidic medium.

22. The process of claim 21 wherein the aqueous acidic medium is 2N to 6N hydrochloric acid.

23. The process of claim 12 wherein R, $R_1$ and $R_2$ are methyl, ethyl or isopropyl.

* * * * *